United States Patent
Yoon et al.

[11] Patent Number: 6,143,005
[45] Date of Patent: Nov. 7, 2000

[54] SUTURING INSTRUMENT WITH ROTATABLY MOUNTED OFFSET NEEDLE HOLDER AND METHOD OF USING THE SAME

[76] Inventors: InBae Yoon, 2101 Highland Ridge Dr., Phoenix, Md. 21131; Samuel C. Yoon, 719 Leister Dr., Timonium, Md. 21093

[21] Appl. No.: 08/847,253

[22] Filed: May 1, 1997

[51] Int. Cl.[7] .................................................. A61B 17/00
[52] U.S. Cl. .............................................................. 606/148
[58] Field of Search .................................... 606/148, 144, 606/139, 145, 147; 112/169, 80.03

[56] References Cited

U.S. PATENT DOCUMENTS

| | | |
|---|---|---|
| 919,138 | 7/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama . |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli . |
| 5,152,769 | 10/1992 | Baber . |
| 5,171,257 | 12/1992 | Ferzli . |
| 5,181,919 | 1/1993 | Bergman et al. . |
| 5,209,741 | 5/1993 | Spaeth . |
| 5,211,650 | 5/1993 | Noda . |
| 5,222,508 | 6/1993 | Contarini . |
| 5,224,948 | 7/1993 | Abe et al. . |
| 5,234,443 | 8/1993 | Phan et al. . |
| 5,244,948 | 9/1993 | Mulhaupt et al. . |
| 5,261,917 | 11/1993 | Hasson et al. . |
| 5,281,238 | 1/1994 | Chin et al. . |
| 5,300,082 | 4/1994 | Sharpe et al. . |
| 5,304,185 | 4/1994 | Taylor . |
| 5,305,121 | 4/1994 | Moll . |
| 5,308,353 | 5/1994 | Beurrier . |

(List continued on next page.)

FOREIGN PATENT DOCUMENTS

| | | |
|---|---|---|
| 482881A1 | 4/1992 | European Pat. Off. . |
| 0337579 | 4/1904 | France . |
| 0395073 | 8/1973 | U.S.S.R. . |
| 2260704 | 9/1991 | United Kingdom . |
| WO 97/37583 | 10/1997 | WIPO . |

*Primary Examiner*—Michael Buiz
*Assistant Examiner*—Vikki Trinh
*Attorney, Agent, or Firm*—Blank Rome Comisky & McCauley LLP

[57] ABSTRACT

An instrument for suturing anatomical tissue with a suture needle includes a barrel having at least one needle holding apparatus therein which can be manipulated from a proximal end of the barrel. Jaws of the needle holding apparatus are offset from a rotatable shaft by a connecting member. In an insertion position, the needle jaws are confined within the diametrical dimension of the barrel at a distal end thereof. After insertion, the jaws can be manipulated to extend beyond the diametrical dimension of the barrel to provide a large working span in which tissue can be sutured.

31 Claims, 10 Drawing Sheets

U.S. PATENT DOCUMENTS

| | | |
|---|---|---|
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. . |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,702,407 | 12/1997 | Kaji . |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. ............ 606/207 |
| 5,810,805 | 9/1998 | Sutcu et al. . |

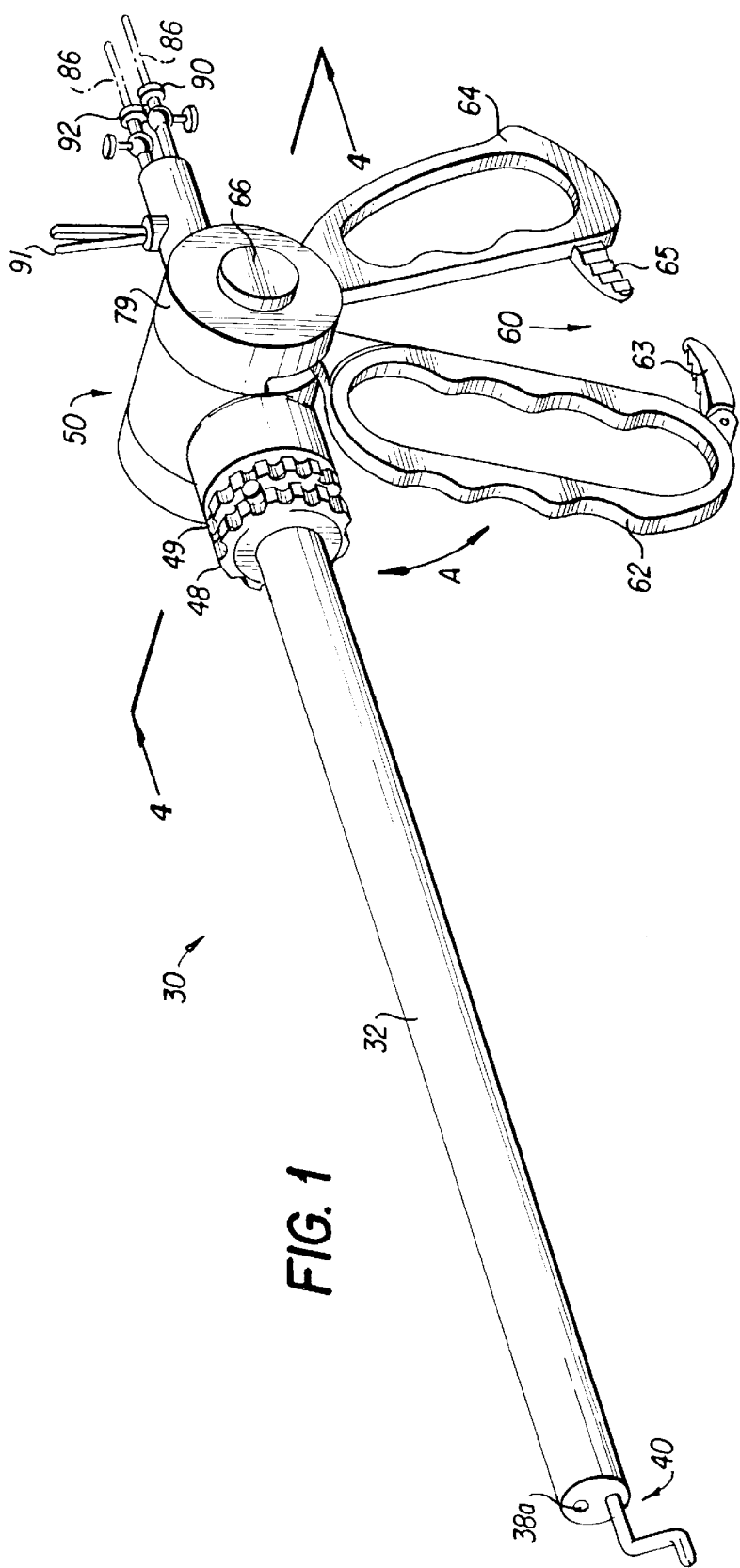
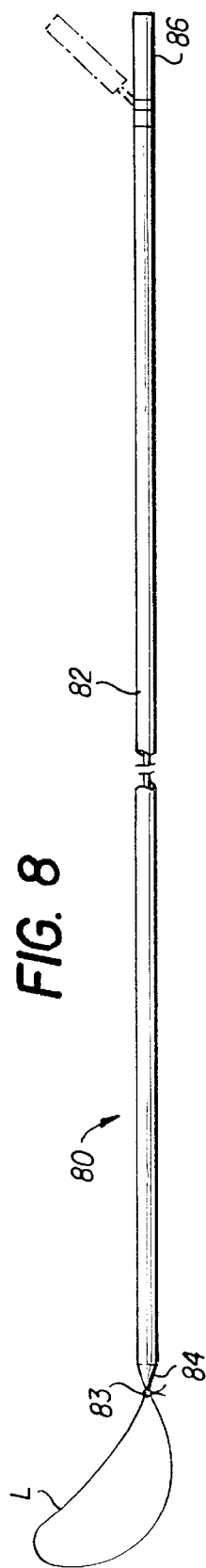
FIG. 1
FIG. 8

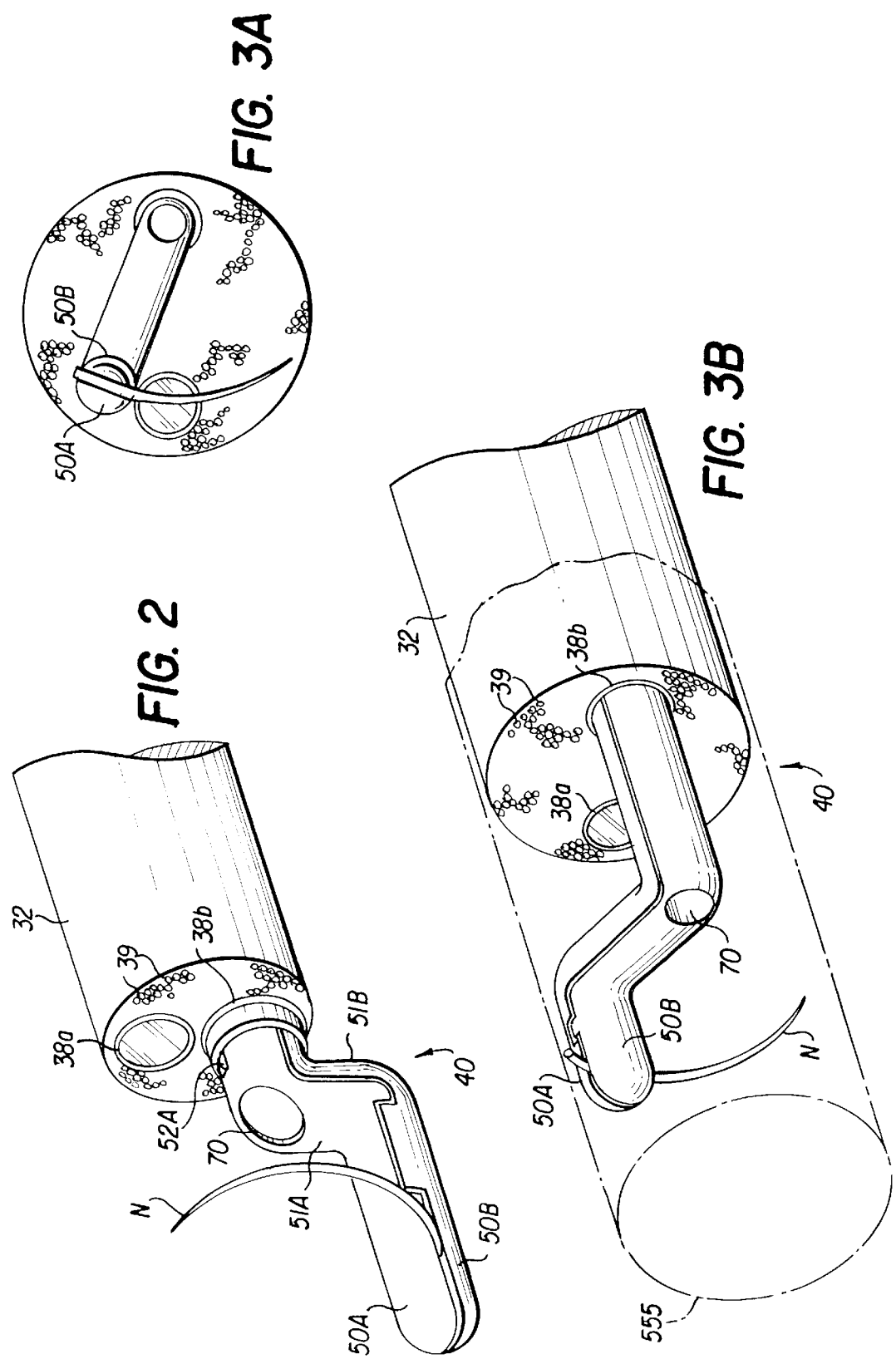

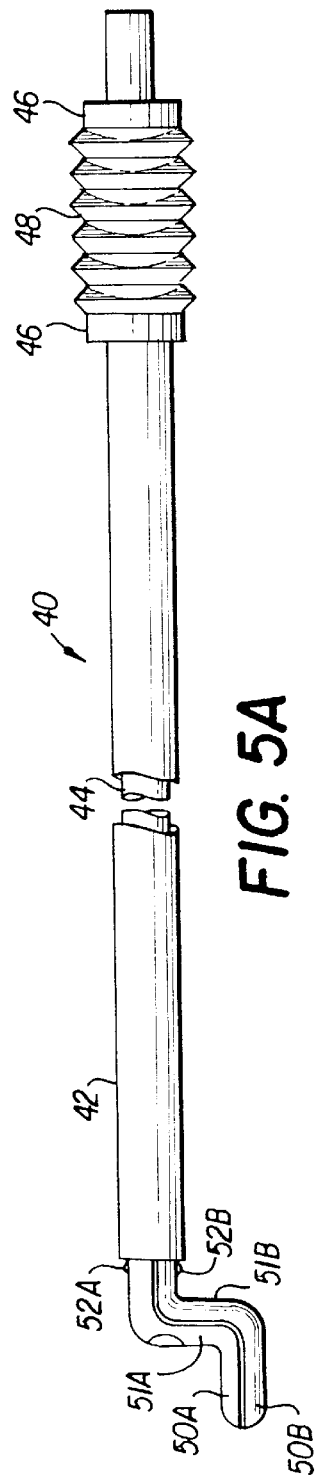

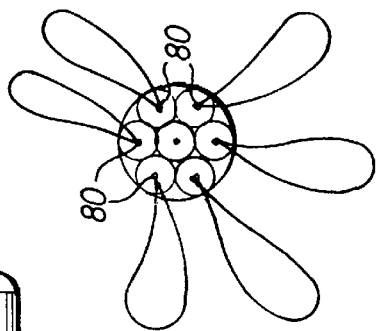
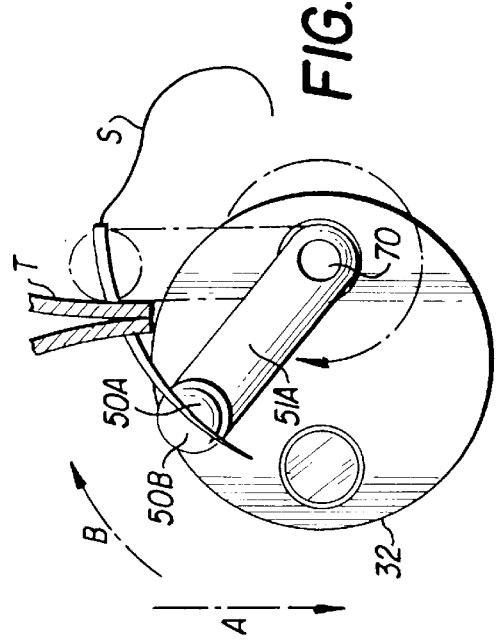
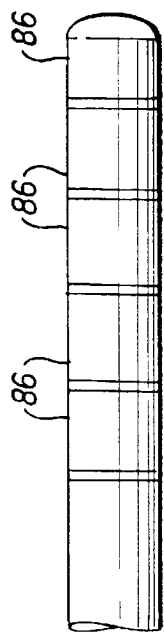
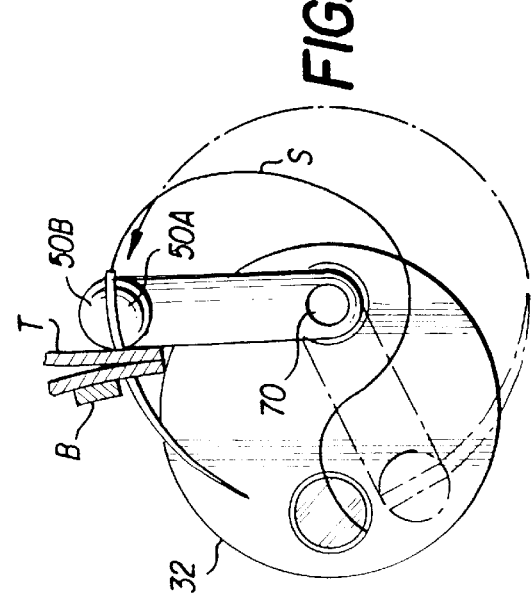
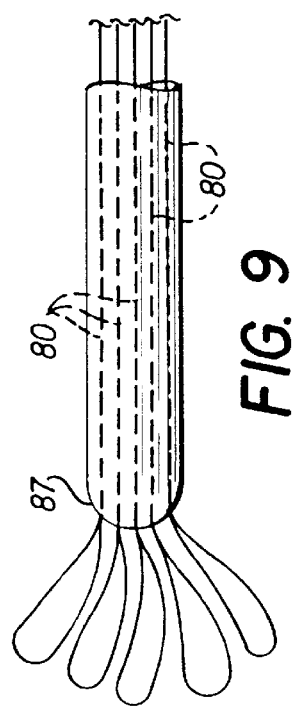

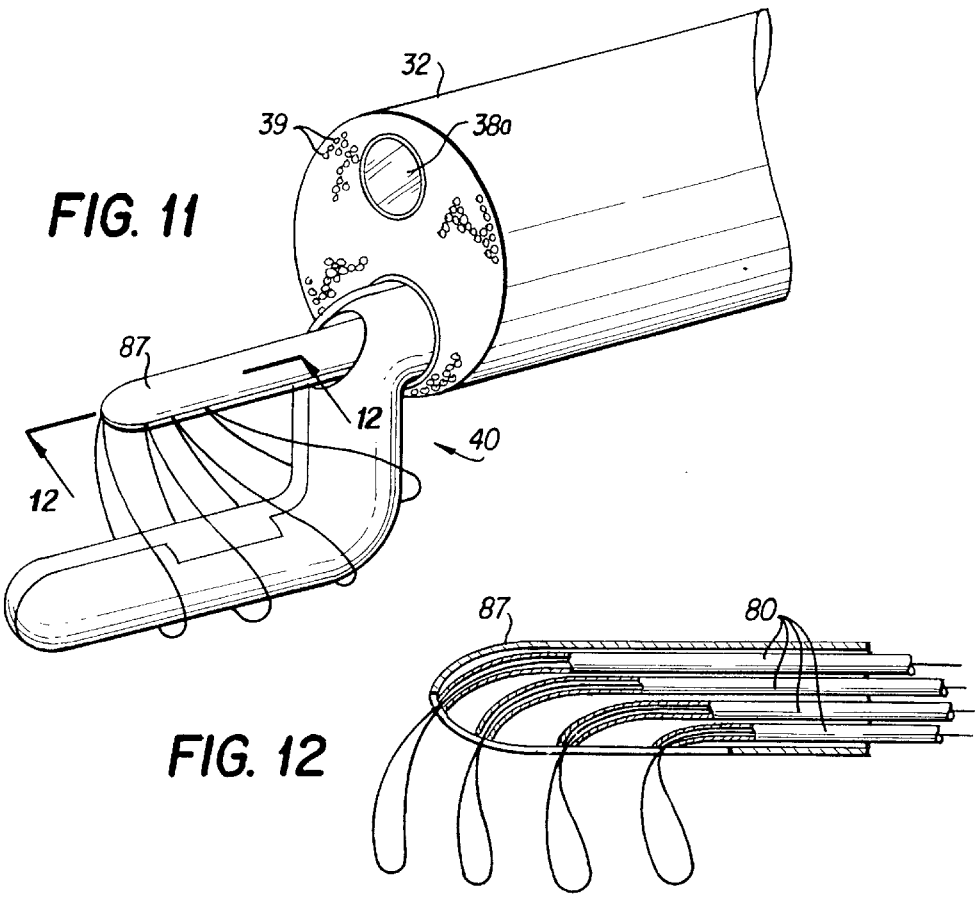
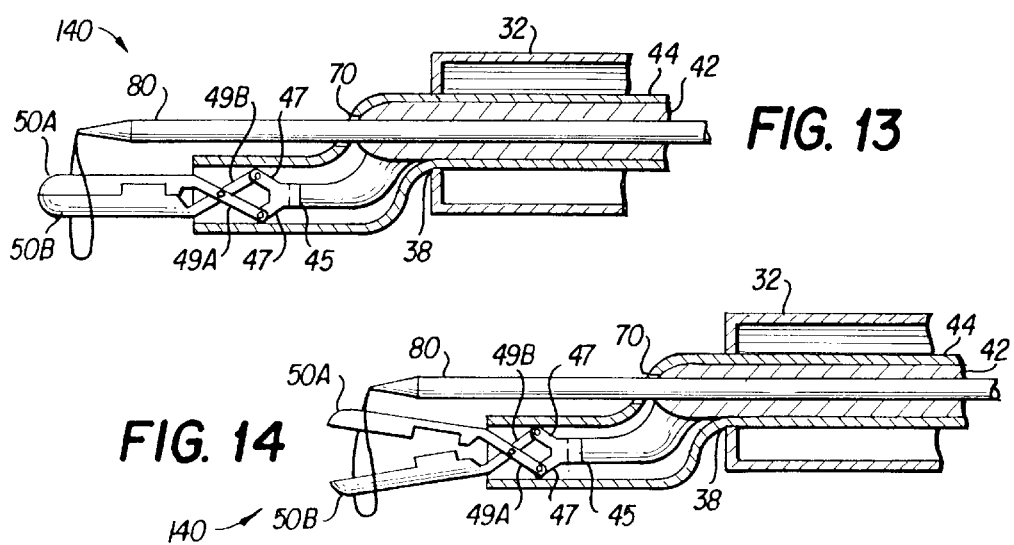

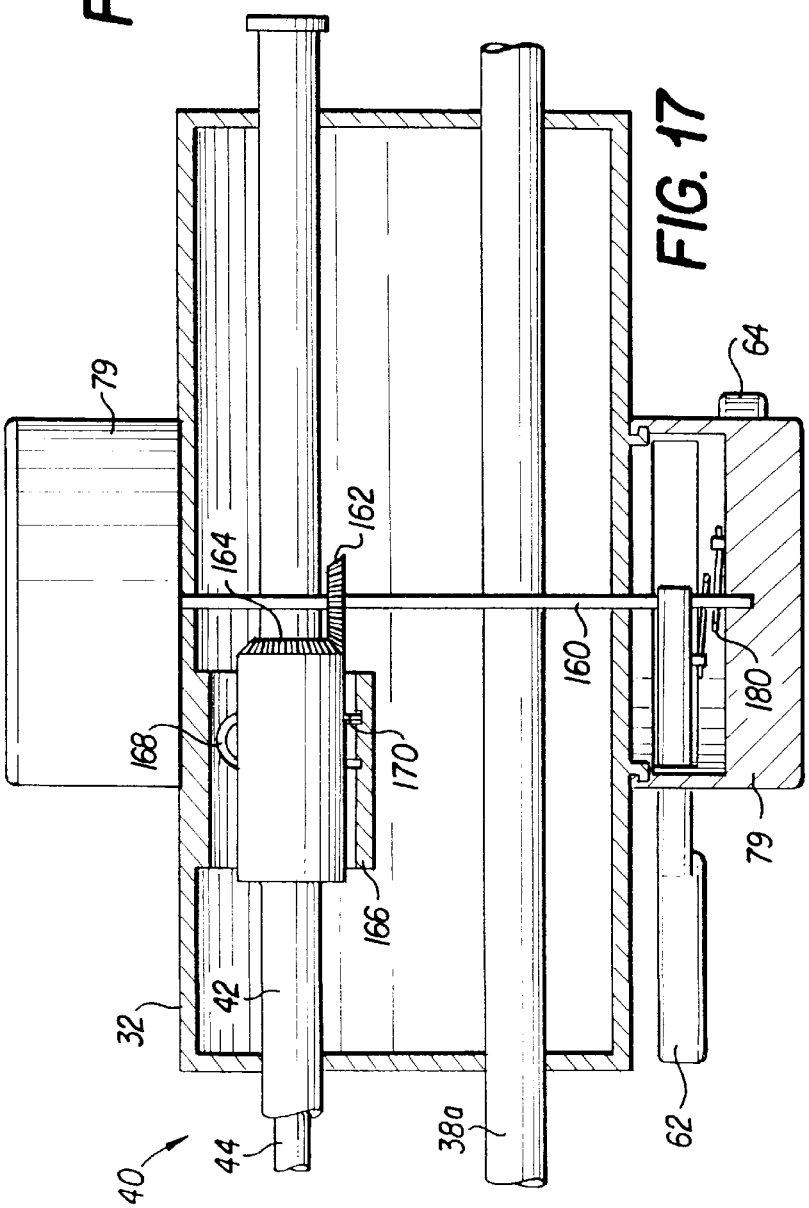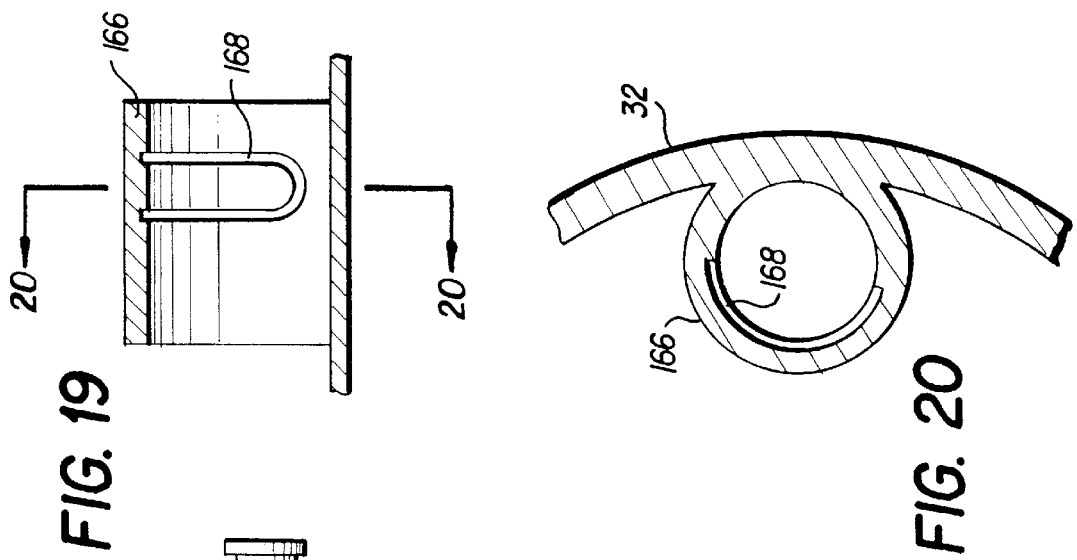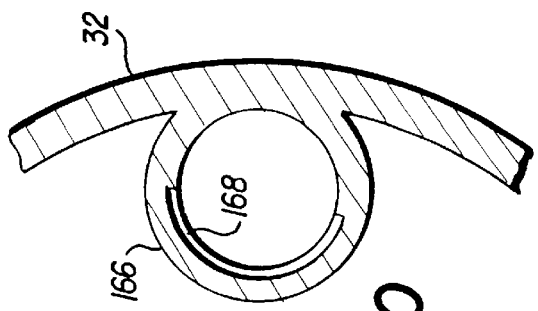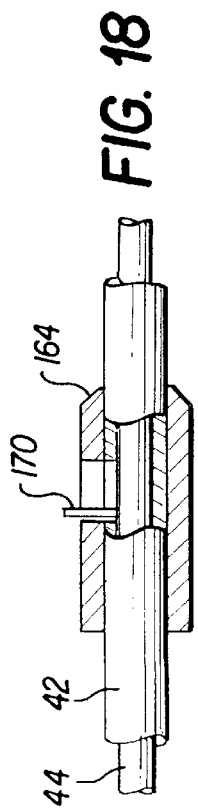
FIG. 19
FIG. 20
FIG. 17
FIG. 18

SUTURING INSTRUMENT WITH ROTATABLY MOUNTED OFFSET NEEDLE HOLDER AND METHOD OF USING THE SAME

RELATED PATENT APPLICATION DATA

This application is related to applicant's copending application Ser. No. 08/366,285 filed on Dec. 29, 1994, Ser. No. 08/377,723 filed on Jan 25, 1995, Ser. No. 08/401,002 filed Mar. 9, 1995, Ser. No. 08/585,875 filed Jan. 16, 1996, and Ser. No. 08/758,648 filed Nov. 27, 1996, the disclosures of which are incorporated herein by reference. Also, this application is related to applicant's concurrently filed applications entitled "Surgical Instrument with Rotatably Mounted Offset End Effector and Method of Using the Same" Ser. No. 08/847,252, "Suturing Instrument with Multiple Rotatably Mounted Offset Needle Holders and Method of Using the Same" Ser. No. 08/847,254, and "Surgical Instrument with Multiple Rotatably Mounted Offset End Effectors and Method of Using the Same" Ser. No. 08/847,189, the disclosures of which are also incorporated herein by reference.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. "Open surgery" refers to surgery wherein the surgeon gains access to the surgical site by a relatively large incision and "endoscopic surgery" refers to minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material. The knotting procedure allows the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers. However, no alternative technique has yet been well accepted by surgeons to produce the results obtained by suturing and knotting. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like (known generally as "end effectors") into the anatomical cavity.

Suturing is typically performed with a needle holding instrument, or needle holder, having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument are opened to release the suture needle so that the tip of the needle can be grasped and pulled through the tissue therewith, or, after opening the jaws, a second needle holding instrument is introduced at the operative site through another portal to grasp the tip of the suture needle after it has emerged from the tissue being sutured. These techniques require difficult manipulation of the needle holder of the suture needle within the jaws of the needle holder before another stitch can be made.

Of course, it is also generally desirable to minimize the size of each puncture site. Further, in order to permit a wide range of tissue sizes to be sutured, it is desirable to provide a needle holder that moves through a path having a large radius of curvature, i.e. a large working span. These objectives, small size of punctures, and a large working span, are seemingly contradictory. Conventional devices have not achieved the above-noted objectives in a satisfactory manner.

SUMMARY OF THE INVENTION

Accordingly, it is a primary object of the present invention to overcome the above-mentioned disadvantages of the prior art and to improve suturing instruments and methods of suturing anatomical tissue.

It is a further object of the present invention to permit a suturing instrument as well as other medical instruments and devices to be introduced through a single portal in an endoscopic procedure without having to withdraw the suturing instrument from the portal.

It is another object of the invention to increase the working span of an endoscopic suturing device and to reduce the insertion diameter while replicating the natural motion of needle passage.

It is another object of the invention to easily manipulate a needle holder during suturing.

Finally, it is an object of the invention to control an endoscopic or open surgical suturing procedure with standard proximal end controls.

The present invention allows suturing of anatomical tissue to be accomplished in a time efficient, consistent and precise manner. Also, suturing can be accomplished using standard suture needles and filamentous suture materials without the need for additional instruments at the operative site.

A first aspect of the present invention is generally characterized in an instrument for suturing anatomical tissue with a suture needle including a barrel, a needle holder having a shaft that is mounted in the barrel for rotation about an axis. The needle holder shaft has needle holding jaw members offset from the axis and selectively operable to grasp and release the suture needle. The jaw members are coupled to the shaft by arms or connecting portions extending from a distal end of the shafts. When the jaw members of the needle holder are operated to grasp the suture needle, the needle holder can be rotated to drive the suture needle through a path having a large radius of curvature to penetrate anatomical tissue. During insertion into an anatomical cavity through a portal or the like, the jaw members are contained within a diametrical dimension of the device. However during suturing, the jaw members can extend beyond this dimension due to the offset configuration.

Another aspect of the present invention is generally characterized in a method of suturing anatomical tissue using a length of suture material attached to a suture needle. The method includes the steps of grasping the suture needle with offset jaw members of a needle holder, rotating the needle holder in a first direction to cause the tip of the needle to penetrate the anatomical tissue, releasing the suture needle from the needle holder, rotating the needle holder in a second direction to grasp the needle tip, and rotating the needle holder in the first direction again to pull the needle and the suture material through the anatomical tissue.

In another aspect of the invention, a needle holder having offset jaw members is combined with a ligating instrument in a single endoscopic device. The ligating instrument carries one or more loops of suture material that can be drawn tightly around a knotting element or the like to secure suture material after the suture material has been passed through the tissue by the needle driver. The ligating instrument is inserted through an operating channel formed in the shaft of the needle holder.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 is a perspective view of the first preferred embodiment of a suturing instrument of the invention;

FIG. 2 is an enlarged perspective view of a distal end of the preferred embodiment in an operating position;

FIG. 3A is an end view of the first preferred embodiment in the insertion position;

FIG. 3B is a perspective view of the distal end of the first preferred embodiment in the insertion position;

FIG. 5A is a side view of a needle holder removed from a barrel of the suturing instrument for illustrative purposes;

FIG. 5B is a partial side view of a first alternative needle holder having pivoting jaw members;

FIG. 5C is a partial side view of a second alternative needle holder having a flexible inner member;

FIG. 5D is a partial side view of a third alternative needle holder that is resiliently flexible;

FIG. 6A is an end view of the distal end of the first preferred embodiment illustrating pushing a needle through tissue;

FIG. 6B is an end view of the distal end of the first preferred embodiment illustrating pulling a needle through tissue;

FIG. 8 is a side view of the ligator for use with the invention; and

FIG. 9 is a side view of the multiple ligator cluster that can be inserted through an operating channel of the first preferred embodiment;

FIG. 10 is an end view cluster illustrated in FIG. 8;

FIG. 11 is an enlarged perspective view of an end portion first preferred embodiment with a multiple ligator cluster inserted through an operating channel;

FIG. 12 is a sectional view of an end of the multiple ligator cluster illustrated in FIG. 11 taken along line 12—12;

FIG. 13 is a sectional view of the distal end of the first preferred embodiment with modified jaws in the closed position;

FIG. 14 is a sectional view of the distal end of the first preferred embodiment with modified jaws in the open position;

FIG. 17 is a sectional view illustrating inner components of an automatic one-handed mechanism;

FIG. 18 is a side view partially in cross-section of a portion of FIG. 17 in detail;

FIG. 19 is an enlarged side view partially in cross-section of a cylindrical member and a cam groove of FIG. 17; and FIG. 20 is a sectional view of FIG. 19 taken along line 20—20.

DETAILED DESCRIPTION OF THE PREFERRED EMBODIMENTS

Figure 4A:
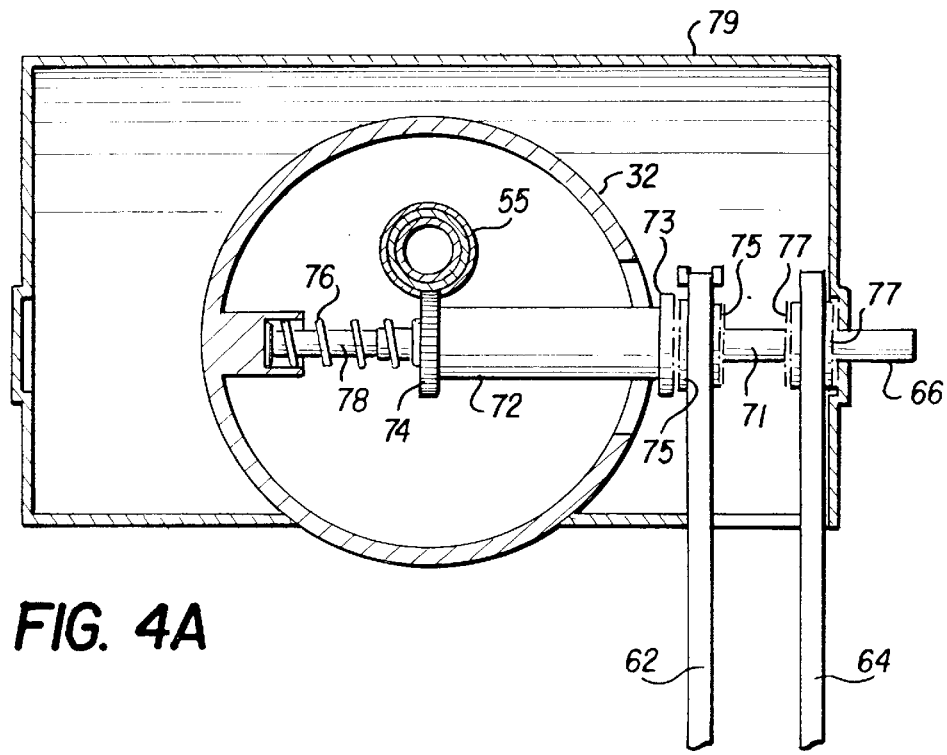
FIG. 4A is a sectional view taken along line 4—4 of FIG. 1 illustrating the inner mechanism of the proximal controls in an operative position.

The suturing instrument of the present invention can be utilized to suture any type of anatomical tissue in any type of anatomical cavity. Accordingly, while the instrument is described hereinafter for use with a portal sleeve in endoscopic procedures, such as laparoscopy, the instrument can be used in open surgery and with catheters and other small and large diameter tubular or hollow cylindrical members providing access to small cavities, such as veins and arteries, as well as large cavities, such as the abdomen.

A suturing instrument according to a first preferred embodiment of the present invention is illustrated at 30 in FIG. 1 and includes cylindrical barrel 32 which has an elongated passage defined therein, and needle holder 40. Needle holder 40 is substantially contained within cylindrical barrel 32 as is described in detail below.

As shown in FIG. 2, barrel 32 includes channels 38*a* and 38*b* extending longitudinally therethrough. Barrel 32 can have additional channels for receiving one or more additional instruments to be introduced in the abdominal cavity or the barrel 32 can have only one channel as needed. A plurality of light transmitting fibers 39 can be disposed in barrel 32 for transmitting light from a proximal light source to an anatomical cavity. Channels 38*a* and 38*b* can be formed by thin wall, tubular sleeves extending longitudinally through barrel 32 or can be merely void spaces defined by light transmitting fibers 39.

FIG. 5. illustrates needle holder 40 removed from barrel 32 for illustrative purposes. Needle holder 40 includes elongated, tubular outer member 42, and elongated tubular inner member 44 disposed within outer member 42. Outer member 42 and inner member 44 define a shaft that is rotatable in barrel 32. Outer member 42 has a proximal end on which two diametrically enlarged flanges 46 are disposed. Flanges 46 serve to fix collar 48 on outer member 42 while permitting collar 48 to rotate with respect to outer member 42. The purpose and function of collar 48 is described below.

Arms 51A and 51B extend from a distal end of inner member 44 to serve as a connecting member between inner member 44 and jaw members 50A and 50B formed on a free end of arms 51A and 51B respectively. A longitudinal axis of jaw members 50A and 50B is offset from a longitudinal axis of the shaft defined by inner member 44 and outer member 42. Jaw members 50A and 50B are normally biased to an open position wherein jaw members 50A and 50B have a gap defined therebetween. This permits the shank of a suture needle to be placed between jaw members 50A and 50B to be grasped thereby. Of course, the inner surfaces of jaw members 50A and 50B can be shaped to correspond to the needle shank, or any other appropriate way, to firmly grasp the needle when the jaw members 50A and 50B are in a closed position as shown in FIGS. 3A and 3B.

Needle holder 40 can be designed in various known ways permitting jaw members 50A and 50B to be movable between the closed position and the open position. For example, the arms 51A and 51B can be made entirely or partly of resilient, flexible or spring materials, or materials having shape memory, to be resiliently biased toward the open position while being movable to the closed position and back to the open position. FIG. 5B illustrates an alternative needle holder 40 having pivoting jaw members 50A and 50B. FIG. 5C illustrates an alternative needle holder 40 having flexible inner member 44 that grasps a needle in a notch formed in outer member 42 when advanced distally. FIG. 5D illustrates another alternative needle holder 40 that is resiliently flexible and can be drawn into barrel 32. In a free state, a distal end of needle holder 40 of FIG. 5D is angled.

Figure 5G:
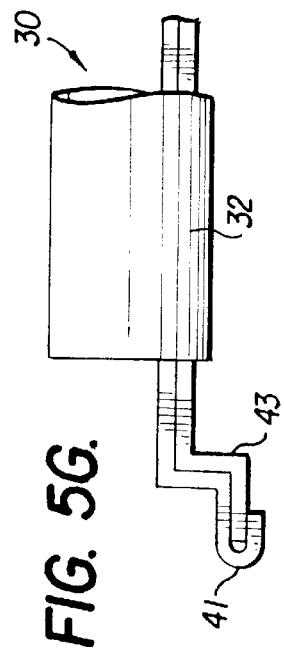
FIG. 5G is a partial side view of a fifth alternative needle holder similar to the fourth alternative needle holder in FIG. 5F except that the fifth alternative needle holder faces outwardly relative to the barrel.
Figure 5H:
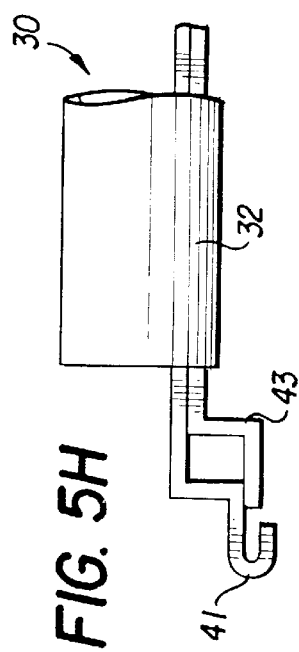
FIG. 5H is a partial side view of the fifth alternative needle holder of FIG. 5G with the sliding keeper in the open position.
Figure 5L:
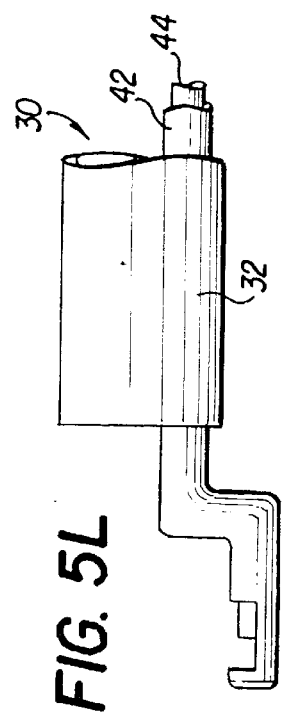
FIG. 5L is a partial side view of a seventh alternative needle holder disposed in the barrel similar to the sixth alternative needle holder except that the hooked member faces inwardly relative to the barrel.
Figure 5E:
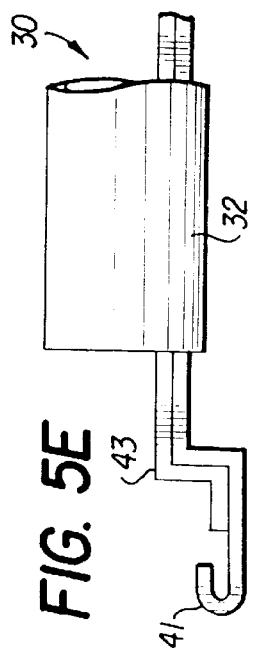
FIG. 5E is a partial side view of a fourth alternative needle holder disposed in the barrel and facing inwardly relative to the barrel with a hooked member and a sliding keeper; and an open position
Figure 5F:
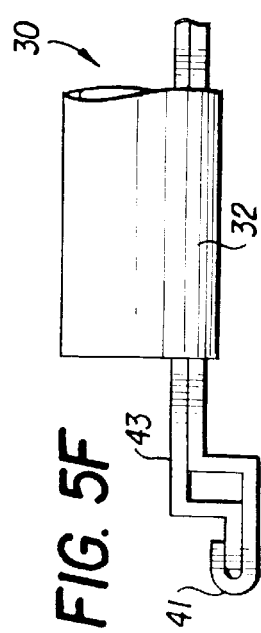
FIG. 5F is a partial side view of the fourth alternative needle holder of FIG. 5E with the hooked member and the sliding keeper in the closed position.
Figure 5K:
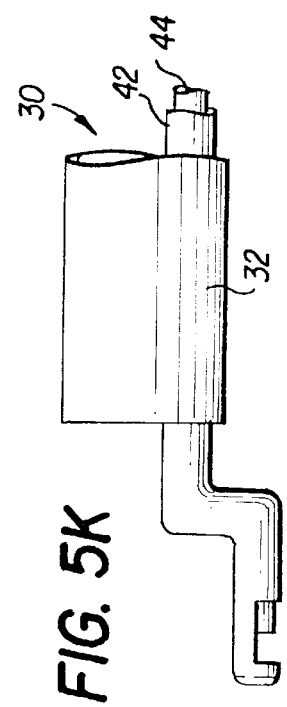
FIG. 5K is a partial side view of a sixth alternative needle holder disposed in the barrel similar to the second alternative needle holder of FIG. 5C except that the hooked member faces outwardly relative to the barrel.

FIG. 5E illustrates a distal end of instrument 30 having a needle holder that includes hooked member 41 and sliding keeper 43 that can be moved distally and proximally with respect to hook member 41. A needle can be grasped when keeper 43 is advanced distally to the closed position illustrated in FIG. 5F. FIG. 5G illustrates a similar arrangement. However, hook member 41 opens outwardly. FIG. 5H shows the open position with keeper 43 withdrawn. FIG. 5K illustrates a distal end of instrument 30 having a needle holder that is configured as illustrated in FIG. 5C. FIG. 5L illustrates a similar configuration. However, in FIG. 5L, the notch in outer member 42 opens outwardly.

Figure 4B:
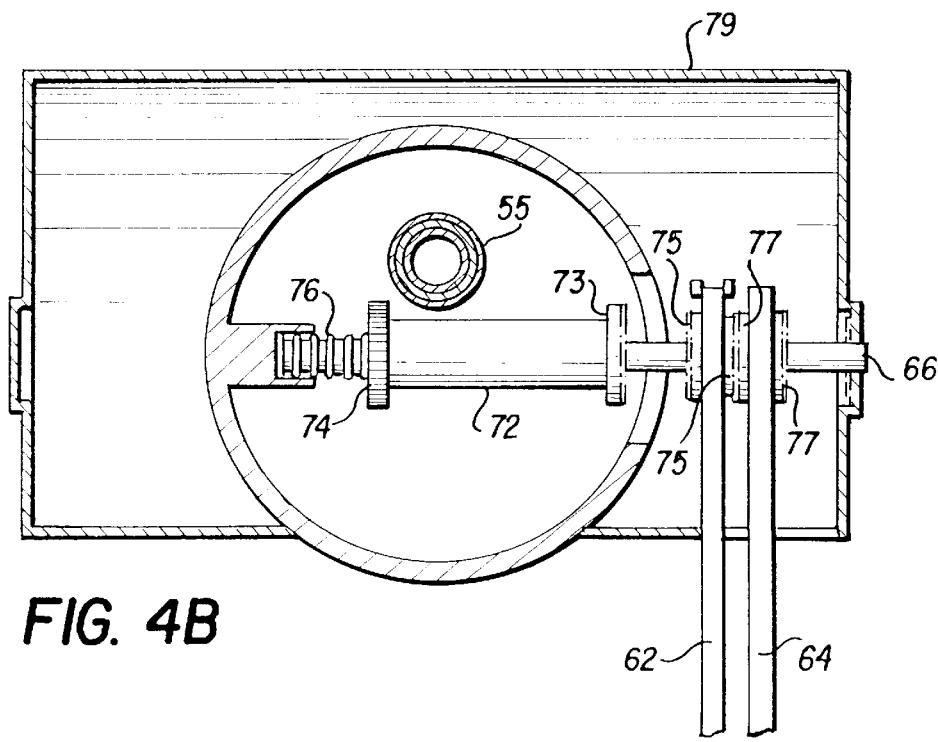
FIG. 4B is a sectional view taken along line 4—4 of FIG. 1 illustrating the inner mechanism of the proximal controls in an adjusting position.

As illustrated in FIG. 1, proximal controls 60 of the preferred embodiment include handles 62 and 64 extending from housing 79 disposed on barrel 32. Button 66 is provided proximate an axis of rotation of handles 62 and 64. Depressing button 66 disengages handles 62 and 64 from needle holder 40 and permits handles 62 and 64 to be rotated in concert about the axis of rotation as indicated by arrow A in FIG. 1. This allows the surgeon to orient handles 62 and 64 in a desired manner prior to or during surgery. FIGS. 4A and 4B illustrate the internal mechanism coupling handles 62 and 64 to needle holder 40. Operating member 72 is rotatably disposed on shaft 71 and has gear portion 74 that is engaged with collar 48 on outer member 42 of needle holder 40. Operating member 72 is fixed axially on shaft 71 and has radially extending serrated teeth 73 formed on a side opposite gear portion 74.

Handle 62 is also rotatably mounted on shaft 71 and is slidable relative to shaft 71. Handle 62 is fixed in axial position by projections formed on an inner surface of housing 79. Handle 62 has radially extending serrated teeth 75 on each side thereof at a top portion that is disposed around shaft 71. Shaft 71 is mounted on stem 78 and is normally biased to the right in FIG. 4A by spring 76 to press serrated teeth 73 into engagement with serrated teeth 75 thus fixing the relative position of operating member 72 and handle 62. Handle 64 is rotatably mounted on shaft 71 and fixed axially on shaft 71. Radially extending serrated teeth 77 are formed on each side of handle 64 at a top portion that surrounds shaft 71 and serrated teeth 77 are normally biased by spring 76 into engagement with teeth formed on an inner surface of housing 79 to fix the position of handle 64 with respect to barrel 32. In this state handle 62 is coupled to collar 55 disposed on outer member 42 of needle holder 40 and handle 64 is fixed in position. Pressing handle 62 towards handle 64 will cause outer member 42 to move over cam surfaces 52A and 52B (see FIG. 5) to close jaw members 50A and 50B.

When shaft 71 is pressed to the left in FIGS. 4A and 4B, by depressing button 66, serrated teeth 77 engage serrated teeth 75 to fix the relative positions of handles 62 and 64 and serrated teeth 73 are disengaged from serrated teeth 75 to disengage handle 62 from needle holder 40, as illustrated in FIG. 4B. This permits the set of handles 62 and 64 to be rotated in concert to the desired orientation without affecting needle holder 40.

As noted above, cam surfaces 52A and 52B are formed on outer surfaces of arms 51A and 51B respectively. When handle 62 pressed towards handle 64, outer member 42 moves distally over cam surfaces 52A and 52B causing jaw members 50A and 50B to move toward one another to the closed position. Cam surfaces 52A and 52B can be formed by bent portions defined in arms 51A and 51B or by separate elements that are attached to, or formed on, legs 51A and 51B. Release of handles 62 and 64 causes jaw members 50A and 50B to return to the open position due to the resilient bias of arms 51A and 51B. Lock protrusions 63 and 65 are disposed on handles 62 and 64 respectively (see FIG. 1) and are serrated to interlock and allow the position of handles 62 and 64 to be maintained in a state corresponding to a desired position of jaw members 50A and 50B. Lock protrusions 63 and 65 can be pivoted to a position of which they will not interlock if desired. Additionally, handles 62 and 64 can be biased apart or outer member 62 can be biased distally or proximally, depending on desired operating characteristics. Also, housing 79 can be rotatable to permit a greater degree of handle adjustment.

The shaft of needle holder 40 is disposed in channel 38b to extend through barrel 32 and can be rotated about a longitudinal axis relative to barrel 32 by rotating collar 48 which is coupled to outer member 42 by a gear or the like. Button 49 is provided to collar 48. Depressing button 49 releases the locked state of collar 48. Collar 48 can be coupled to needle holder 40 in any appropriate manner, such as by a gear as disclosed in the copending application entitled "Surgical Instrument with Multiple Rotatably Mounted Offset End Effectors and Method of Using the Same", the disclosure of which is incorporated herein by reference.

A known optical observation device, such as an optical endoscope using fiber optics or a CCD device for transmitting an image from the distal end to the proximal end, can be inserted in channel 38a, through proximal aperture 92 (see FIG. 1), for permitting observation of the operation of the other elements. Additional channels can be provided for a suction device, an irrigation device, or any other appropriate instrument.

In use, suturing device 30 is inserted into a body cavity using known techniques, while needle holder 40 is in the insertion position, or parked position, illustrated in FIGS. 3A and 3B. Note that the entire device can be inserted through a single puncture site. Also, in the insertion position, jaw members 50A and 50B as well as needle N are disposed within the diametrical dimension of barrel 32 because of the position of arms 51A and 51B. The distal end of suturing device 30 is guided to the operative site through a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. A retractable tubular sheath 555 (shown with dotted lines in FIG. 3B), or any other appropriate structure, can cover the distal end during insertion to facilitate insertion and prevent damage to a valve housing or the like. Visualization of the endoscopic procedure can be accomplished using a conventional endoscope incorporated into the channel 38a as noted above (i.e. a single puncture operation) or separately positioned within the anatomical cavity through a second portal sleeve located at another puncture site (i.e. a double puncture operation).

During insertion, needle N is held tightly between jaw members 50A and 50B of needle holder 40. A detent device, such as serrated projections 63 and 65 illustrated in FIG. 1, can be provided to selectively maintain jaws 50A and 50B in a position holding the needle while freeing the operator's hands for other manipulation. Alternatively, needle N can be introduced into the body cavity by a separate instrument through a separate puncture sight. In this embodiment, needle N is of a semi-circular configuration. However, needle N can be straight or of any other appropriate shape.

Referring now to FIGS. 6A and 6B, which illustrate a suturing process, the shaft of needle holder 40 is rotated, by rotating collar 48 or barrel 32, from the insertion position, in a counter-clockwise direction, as viewed in FIGS. 6A and 6B to the position indicated by the dotted line in FIG. 6A. A backing device B is placed behind tissue T to support tissue T. Backup device B can be inserted through a separate portal or the like or can be inserted through operating channel 38a or another operating channel formed in barrel 32, or can be fixed to barrel 32. Subsequently, the shaft of needle holder 40 is rotated further in a counter-clockwise direction, by rotating collar 48 or barrel 32, to drive a tip of needle N through a portion of the tissue T while the tissue T is supported from an opposite side by backup device B as illustrated by the solid lines in FIG. 6A.

Jaw members 50A and 50B are then placed in the open position, by releasing lock protrusions 63 and 65 or otherwise permitting handles 62 and 64 to separate, and thus needle N is released from jaw members 50A and 50B of needle holder 40. Subsequently, the shaft of needle holder 40 can be rotated in a clockwise direction, by rotating collar 48 or barrel 32, to receive the shank of needle N once again at the position shown by the solid lines in FIG. 6B. The shaft of needle holder 40 can then be rotated back in the counter-clockwise direction to pull needle N, and suture material S that is connected to needle N, through tissue T to complete a stitch. The movement of the needle is through an arcuate path that extends beyond the diameter of barrel 32 as indicated by the dotted line in FIG. 6A. This provides a large working span. Also, this movement can be accomplished merely by rotating a single shaft. Alternatively, the entirety of barrel 32 can be rotated to move the jaw members while needle holder 40 is locked in position relative to barrel 32. For a subsequent stitch, needle holder 40 can be rotated in the counterclockwise direction to the other side of tissue T or barrel 32 can be moved away from tissue T (in the direction of arrow A) and needle holder 40 can be rotated in a clockwise direction to the other side of tissue T, as indicated by arrow B. Of course needle N can be positioned to permit left-handed operation, i.e. stitching in the opposite direction.

At any point during the operative procedure, channel 38a can be used for irrigation or aspiration, can serve as a space for holding the suture material or as a portal for the introduction of other medical instruments such as, forceps, cutting members, endoscopes or ligators. Also, additional channels can be formed for irrigation, aspiration, or the like. Further, the passage through inner member 44 of the needle holder 40 can be used as an operating channel, accessed through proximal aperture 90, because aperture 70 is formed in arm 51A.

Needle holder 40 can be modified to suture anatomical tissue with straight or slightly curved suture needles by shaping jaw members 50A and 50B appropriately to receive and hold the needle. Also, jaw members 50A and 50B can be rotatable on arms 51A and 51B to accept needle N more smoothly. Further, known knotting elements can be used in lieu of traditional knotting techniques during the suturing procedure. Some examples of suitable knotting elements for this purpose are described in pending applications Ser. No. 08/366,285, filed Dec. 29, 1994; Ser. No. 08/377,723, filed Jan. 25, 1995; Ser. No. 08/401,002, filed Mar. 9, 1995; and Ser. No. 08/585,875, filed Jan. 16, 1996, the disclosures of which are incorporated herein by reference. In addition, if both axial ends of needle N are provided with sharp, tissue penetrating tips, it is possible to penetrate the anatomical tissue at multiple locations in order to form a continuous run of stitches merely manipulating the needle in a "shuttle" manner, i.e. passing the needle through the tissue in alternating directions.

From the above, it will be appreciated that the suturing instrument according to the present invention permits suturing of anatomical tissue during endoscopic procedures without the need for difficult manipulation of the instrument. The needle holder is operable to grasp and release a suture needle so that the suture needle can be driven through anatomical tissue, and can be moved to pull the suture material through the anatomical tissue with a large working span.

Figure 7A:
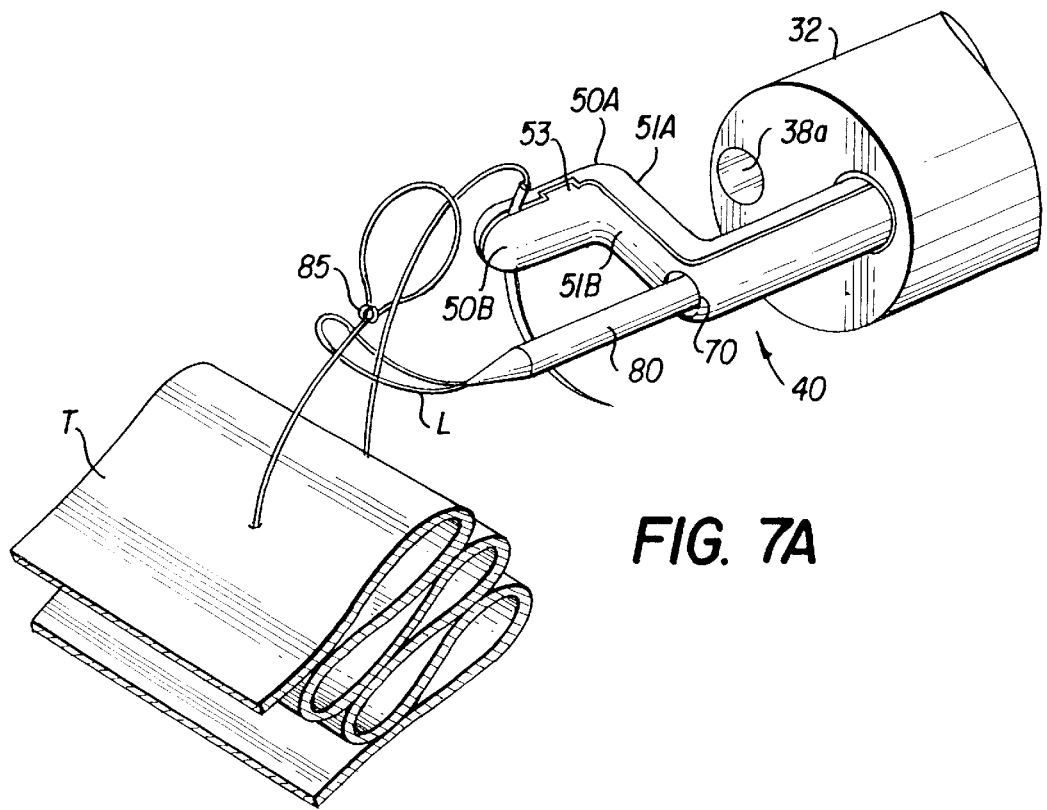
FIG. 7A is a perspective view of the distal end of the first preferred embodiment used in combination with a ligator for suturing.
Figure 7B:
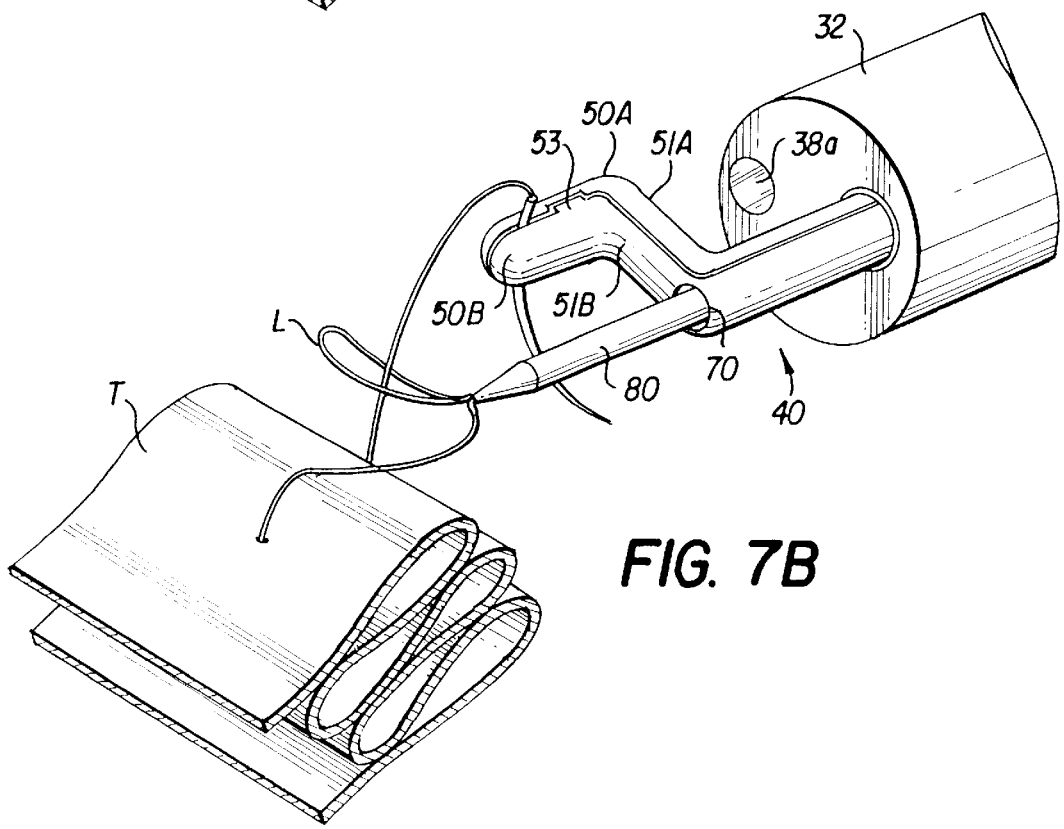
FIG. 7B is a perspective view of the distal end in combination with an alternative ligator.

As illustrated in FIG. 7A, an instrument such as ligator 80 can be inserted from the proximal end of barrel 32 of suture device 30 through an operating channel defined through needle holder 40, through proximal aperture 90, to extend out of aperture 70 at the distal end of needle holder 40 as illustrated in FIGS. 7A and 7B. FIG. 8 illustrates ligator 80 removed from barrel 32 for illustrative purposes. Ligator 80 consists of tubular member 82 having tapered portion 84 at a distal end and handle 86 at a proximal end. A length of suture material extends through tubular member 82. One end of the suture material is fastened to handle 86. The other end of the suture material extends out of an opening formed in tapered portion 84 and is formed into loop L by slip knot 83 formed at an end portion of the suture material and around a portion of suture material near tapered portion 84. The opening in tapered portion 84 is large enough to permit unknotted portions of the suture material to pass therethrough but not large enough to permit slip knot 83 to pass therethrough.

Handle 86 can be separated from tubular member 82 as shown by the dotted line in FIG. 8. Handle 86 can extend from proximal aperture 90 at a proximal end of suturing device 30, as illustrated by the dotted line in FIG. 1. Therefore handle 86 can be manipulated by the surgeon. In particular, handle 86 can be pulled away from tubular member 82 to pull suturing material through slipknot 83 to thereby reduce the size of loop L. This can facilitate knotting of suture material that has been pulled through the tissue by needle holder 40 as is described below.

During a suturing process, a shank of needle N is grasped between jaw members 50A and 50B of needle holder 40. A length of suturing material is attached to the shank and a loop is formed on a free end of the suturing material by knotting element 85 as illustrated in FIG. 7A. Needle holder 40 is pivoted, by rotating its shaft in the manner disclosed above, to pass needle N through the tissue to be sutured, such as the folded vaginal wall tissue T illustrated in FIG. 7A. Needle holder 40 then releases the shank of needle N and is pivoted in the reverse direction to pass to the other side of folded tissue T where needle holder 40 is operated to grasp the shank of needle N that has passed through tissue T in the manner disclosed above. Needle holder 40 is then pivoted to pull needle N entirely through tissue T. Subsequently, needle holder 40 is manipulated to pull needle N through loop L of suture material on the end of ligator 80 to the position illustrated in FIG. 7A (in which the tissue has been moved relative to the instrument for clarity). Needle holder 40 can be movable axially in barrel 32 as disclosed in the copending application entitled "Surgical Instrument with Multiple Rotatably Mounted Offset End Effectors and Method of Using the Same", the disclosure of which is incorporated herein by reference. This facilitates passing needle N through loop L.

Then, needle holder 40 can be manipulated to pull suture material snugly into tissue T and seat knotting element 85 against one side of tissue T. Subsequently, loop L can be tightened around the suture material on the other side of tissue T by pulling on handle 86. This secures the suture material against the other side of tissue T so that the suture material cannot pass back through tissue T. The suture material can then be cut from needle N and ligator 80 by cutting elements 53 formed in the jaws of needle holder 40.

FIG. 7B illustrates an alternative arrangement in which the suture material connected to the needle extends from slip Knot 83 forming loop L. This arrangement is otherwise similar to the arrangement of FIG. 7A and is operated in a similar manner.

Also, a plurality of ligators 80 can be inserted in a cluster through an operating channel to permit multiple portions of tissue to be sutured, as illustrated in FIG. 10. As illustrated in FIGS. 9 and 12, the plural loops of ligators 80 can all extend through a slot formed in sheath 87 that covers and end of a cluster of ligators 80. Also, handles 86 for the plural ligators can be disposed in seriatim along a proximal end of the ligator cluster as illustrated in FIG. 9. Each handle 86 can then be separated to manipulate the corresponding loop one at a time. FIGS. 9 and 10 show a ligator cluster in which the ligators 80 all extend to the distal end of the cluster. FIGS. 11 and 12 show a ligator cluster in which the ends of the ligators 80 are staggered to permit each loop to extend downward without interfering with the other loops. Alternatively, a plurality of ligators can extend from different operating channels A lock device can be provided to selectively lock the ligators in position.

This embodiment can utilize proximal end controls similar to those discussed above with respect to the first preferred embodiment or can include a "pistol-grip" handle at the proximal end thereof similar to that disclosed in application Ser. No. 08/758,648, the disclosure of which is incorporated herein by reference. Also, the proximal controls the copending application entitled "Surgical Instrument with Multiple Rotatably Mounted Offset End Effectors and Method of Using the Same", the disclosure of which is incorporated herein by reference, can be used.

The preferred embodiment disclosed above has jaw members that are biased to an open position and operated by interaction between a cam and the outer member. The modification illustrated in FIGS. 13 and 14 uses pivoting jaw members. Needle holder 40 is disposed within operating channel 38a in barrel 32. Needle holder 40 includes outer member 42, inner member 44 disposed in outer member 42, and jaw members 50A and 50B coupled to a distal end of inner member 44. Outer member 42 has a bent perpendicular segment disposed perpendicularly or angularly to a main body of the outer member and an offset distal segment extending from the angled segment and disposed parallel to the main body of the outer member 42. Both the bent segment and the distal segment extend out of a distal end of barrel 32. An operating channel extends entirely through the outer member 42 including the bent segment and the distal segment and terminates at aperture 70.

Inner member 44 includes a main body disposed in the main body of outer member 42, a bent perpendicular segment disposed in the bent segment of outer member 42 and a Y-shaped segment 45 disposed in the distal segment of outer member 42. A passage extends entirely through the main body of inner member 44 in axial or longitudinal alignment with aperture 70 formed in the angled segment of the outer member 42 such that ligator 80, or another instrument, can pass therethrough. The bent segments correspond to the arm or connecting member of the embodiment discussed above.

Y-shaped segment 45 has outwardly extending portions 47 that are pivotally connected to legs 49A and 49B extending from jaw members 50A and 50B, respectively. Legs 49A and 49B are angled inwardly from their respective jaw members to overlap one another in cross-wise fashion. Proximal ends of legs 49A and 49B are pivotally connected to extending portions 47, respectively, at pivots. These pivots also permit extending portions 47 to slide axially along legs 49A and 49B. Legs 49A and 49B are pivotally connected to one another, where they overlap, by a pivot. This pivot is fixedly secured to outer member 42 such that the pivot cannot move longitudinally. Inner member 44 is slidably disposed in outer member 42 to permit longitudinal movement relative thereto.

There is adequate clearance between the bent segment of inner member 44 and the bent segment of outer member 42 to permit inner member 44 to be moved longitudinally, relative to outer member 42. When inner member 44 is moved in the proximal direction, jaw members 50A and 50B are placed in the closed position by the pivoting motion of legs 49A and 49B, as illustrated in FIG. 13. On the other hand, when inner member 44 is moved in the distal direction, jaw members 50A and 50B are placed in the open position by the pivoting motion of legs 49A and 49B, as illustrated in FIG. 14. Of course, movement of inner member 44 can be accomplished by proximal end controls in the manner disclosed above with respect to the first and second embodiments, or in any other appropriate manner. Slots can be formed in a distal end of outer member 42 to permit ends of legs 49A and 49B to extend out of outer member 42, in a radial direction thereof, when jaws 50A and 50B are in the open position, if necessary. This permits a greater stroke of jaw members 50A and 50B.

Figure 15A:
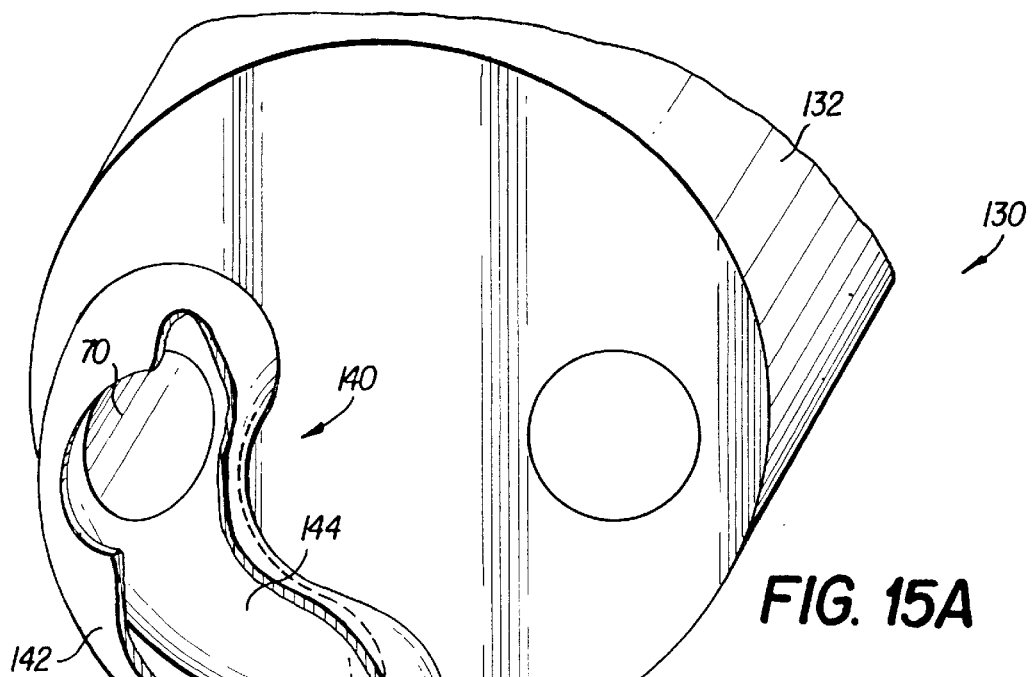
FIG. 15A is an enlarged perspective view, in partial section, of a distal end of the second preferred embodiment.
Figure 15B:
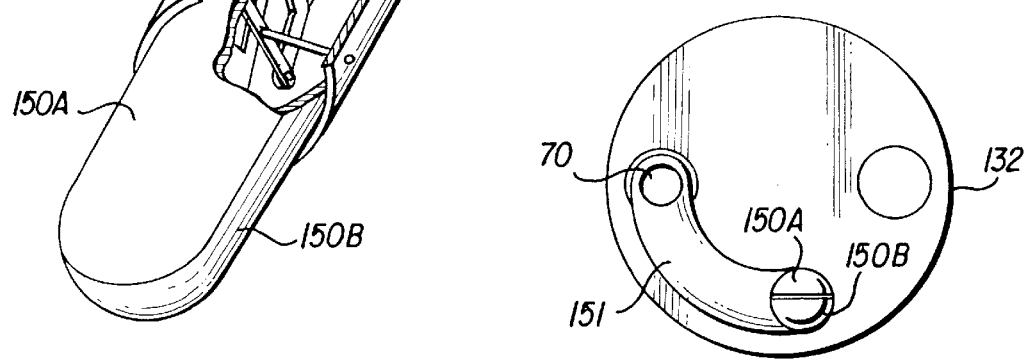
FIG. 15B is an end view of the second preferred embodiment.

A suturing instrument according to a second preferred embodiment is illustrated at 130 in FIGS. 15A and 15B. This embodiment includes needle driver 140 and is similar to the second preferred embodiment except for the configuration of the bent segments of inner member 144 and outer member 142. In particular, the bent segments are curved to correspond substantially with the curvature of the circumferential outer surface of barrel 132. Jaw members 150A and 150B are moveably mounted on a distal end of outer member 142 to open and close in a manner similar to the jaw members disclosed above in FIGS. 13 and 14. Jaw members 150A and 150B can be similar to the jaw members illustrated in FIG. 5 also.

As is best illustrated in FIG. 15B, arm 151 can easily be confined within the diametrical dimension of barrel 132 during insertion. During suturing, or other procedures, jaws 150A and 150B can be moved, by rotating the shaft defined by inner member 144 and outer member 142, to cause jaw members 150A and 150B to be moved through a path that is outside of the diametrical dimension of barrel 32. Rotation of the shaft can be accomplished in a manner similar to the first embodiment described above.

Figure 16:
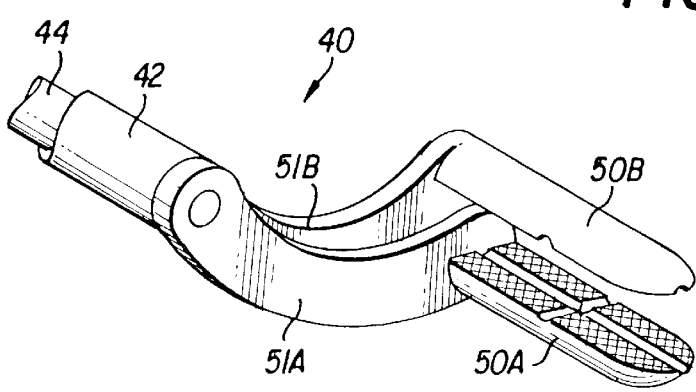
FIG. 16 is a perspective view of a distal end of an eighth alternative needle holder.

FIG. 16 illustrates an alternative needle holder 40 in which arm member 51A is mounted on inner member 44 and arm member 51B is mounted on outer member 42. Jaws 50A and 50B can be opened by rotating inner member 44 and outer member 42 relative to one another. Rotating outer member 42 and inner member 44 in concert will permit a needle to be advanced through an arcuate path. Also, longitudinal and transverse grooves are formed in the jaws to facilitate grasping the needle.

To permit one-handed operation of suturing instrument 30 the motion of needle holder 40 can be accomplished automatically. In particular, handles 62 and 64 can be coupled to needle holder 40 in a manner which causes the desired rotation of the shaft of needle holder 40 and the opening and closing operation of the jaws necessary for a single stitch, or multiple stitches, to be effected merely by squeezing and releasing handles 62 and 64 once or multiple times. The mechanism coupling handles 62 and 64 to needle holder 40 can be designed to accomplish any of the stitching functions disclosed above or any other appropriate motion. Such an automatic mechanism facilitates suturing by minimizing fatigue on the surgeon and reducing the possibility of operational errors.

An example of an automatic mechanism is illustrated in FIGS. 17–20. As illustrated in FIG. 17, handle 64 is fixed to housing 79 and handle 62 is rotatably disposed on shaft 160. Beveled gear 162 is also disposed on shaft 160 and is engaged with beveled gear 164 disposed on outer member 42. Accordingly, compression of handle 62 toward handle 64 causes outer member 42 to rotate. Inner member 44 is constructed to rotate with outer member 42.

As best illustrated in FIGS. 18–20, projection 170 extends from inner member 44 through slots formed in outer member 42 and beveled gear 164. A free end of projection 170 slides along cam groove 168 formed in cylindrical member 166. Therefore, as inner member 44 rotates, inner member 44 is moved axially relative to outer member 42, causing jaws of needle holder 40 open or close.

In operation, a needle is grasped in the jaws of needle holder 40 in the position illustrated in FIG. 17. Handle 62 is squeezed toward handle 64, by the surgeon, causing needle holder 40 to turn clockwise, as viewed from the distal end of the suturing instrument. As needle holder 40 completes a stroke, thus driving the needle through tissue, the jaws are opened by projection 170 as it follows cam groove 168. With the jaws opened, handle 64 can be released causing needle holder 40 to rotate counter-clockwise, as viewed from the distal end as projection 170 continues in the same direction along cam groove 168 to maintain the open position of the jaws. The jaws of needle holder 40 can now be positioned around the tip of the needle that has penetrated the tissue. Compressing the handles again will close the jaw and pull the needle through the tissue. Of course, cam groove 168 can be shaped in various ways to provide the desired opening and closing of the jaws.

The jaw members can be configured to hold any type of needle including, but not limited to, straight and curved needles. One or more lengths of suture material can be attached to each suture needle at any desirable location along the body or tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body.

The holding mechanism of the needle driver apparatus shown and described herein is merely exemplary of the types of needle holding mechanisms that can be used according to the present invention. Accordingly, the jaw members and other components can have any suitable configuration for cooperatively grasping needles to suture anatomical tissue including, but not limited to, configurations wherein the jaw members pivot, slide or otherwise move relative to one another to capture and release a needle. The jaw members can, for example, be of straight, curved or angled configuration and can be provided with ribs, grooves, slots and/or holes along grasping surfaces to assure a positive grip. The jaw members can also carry cutting members, such as slots with sharp edges or protruding blades, and can have opposed arcuate or concave portions for clamping tubular objects, such as organs, without compressing the objects.

The mechanisms for moving the driver apparatus is merely exemplary of the types of mechanisms that can be used to perform this function and other mechanisms can be used. The particular length and curvature of the suture needles shown and described herein as well as any angular displacements of the needle driver apparatus shown and described herein are merely exemplary, and it will be appreciated that other needle lengths and angular displacements can be used. Also, the needle driver apparatus can be movable in the proximal and distal directions.

The needle holder can be used as forceps, to grasp the tissue, before or after suturing or can include a clip applicator. Therefore the invention can be used for pickup and cutting, pickup and clipping, pickup and suturing, or lysis of adhesion procedures. Alternatively, a forceps device can be inserted through the operating channel formed in the shaft of one of the needle holders or another operating channel. Also, blade members on the jaws can be used for cutting tissue. Electrical connector 91 can serve to couple the jaws or any other instrument to an electrical power source to permit unipolar or bipolar cauterization. Also, the jaws can be placed on either side of tissue to manipulate the tissue without grasping it by pushing the tissue.

The components of the suturing instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A suturing instrument for causing a needle to pass through anatomical tissue comprising:
    an elongated barrel having a distal end and a proximal end;
    a handle coupled to said proximal end of said barrel;
    a connecting member coupled to a distal end of said barrel;
    and needle holding members extending from said connecting member, said needle holding members having a longitudinal axis that is offset from a longitudinal axis of said shaft and being operable by said handle to grasp the needle;
        wherein said connecting member is rotatably coupled to said barrel to move said connecting member between a first position, in which said needle holding members are contained entirely within a diametrical dimension of said barrel, and a second position, in which at least a portion of said needle holding members extend beyond the diametrical dimension of said barrel.

2. An instrument as recited in claim 1, wherein said connecting member is coupled to said barrel to rotate about a first axis that is substantially parallel to the longitudinal axis of said barrel.

3. An instrument as recited in claim 2 wherein said connecting member comprises an arm extending from a distal end of said barrel in a direction that is substantially perpendicular to the longitudinal axis of said barrel.

4. An instrument as recited in claim 3 wherein said arm comprises a pair of arm members, said instrument further comprising an opening device for moving said jaw members toward and away from one another.

5. An apparatus as recited in claim 4, further comprising: an operating channel defined in said shaft and extending from said proximal end to said distal end.

6. An instrument as recited in claim 5, further comprising:
    a ligator for tightening a suture loop around a piece of suture material, said ligator being disposed in said operating channel.

7. An instrument as recited in claim 1, further comprising an operating channel defined in said barrel and extending from said proximal end to said distal end.

8. An instrument as recited in claim 7, further comprising:
    a ligator for tightening a suture loop around a piece of suture material, said ligator being disposed in said operating channel.

9. An instrument as recited in claim 1, wherein said connecting member is arcuate.

10. A method of suturing anatomical tissue using a length of suture material attached to a needle, said method comprising the steps of:
    introducing an instrument having a barrel into an area proximate the anatomical tissue;
    grasping the needle with a needle grasping device, the needle grasping device comprising a connecting member coupled to a distal end of said barrel and extending transversely from said distal end of said barrel, and needle holding members disposed on a free end of said connecting member and being operable from a proximal end of said barrel to grasp the needle;
    rotating the connecting member in a first direction about an axis parallel to the longitudinal axis of the barrel to cause the needle to move in an arcuate path and to cause a tip of the needle to penetrate the anatomical tissue; and
    releasing the needle from the needle holding members.

11. A method as recited in claim 10, wherein said rotating step comprises rotating the barrel.

12. A method as recited in claim 10, further comprising the steps of:
    after releasing the suture needle from the needle holding members, rotating the connecting member in a second direction that is opposite to the first direction to receive a tip of the needle in the needle holding members;
    grasping the needle in the needle holding members again; and
    rotating the connecting member in the first direction to pull the needle through the tissue.

13. A method as recited in claim 12, further comprising the steps of:

inserting a ligator having a loop through an operating channel defined in the barrel;

pulling the needle through the loop; and tightening the loop around the length of suture to secure the suture to the tissue.

14. A method as recited in claim 13, wherein the suture material attached to the needle extends from a knotting element that defines the loop.

15. A method as recited in claim 12, further comprising the steps of:

moving the barrel in an axial direction; and rotating the connecting member in the second direction to penetrate the tissue again.

16. A method as recited in claim 12, further comprising the steps of:

moving the barrel away from the tissue; and rotating the connecting member in the second direction to move the needle to the other side of the tissue for a subsequent stitch.

17. A suturing instrument for causing a needle to pass through anatomical tissue comprising:

an elongated barrel having a distal end and a proximal end;

a handle coupled to said proximal end of said barrel;

a connecting member coupled to the distal end of the barrel and extending perpendicularly from the distal end of said barrel; and needle holding members disposed on said connecting member and operable by said handle to grasp the needle;

wherein said connecting member is moveably coupled to said barrel to move said connecting member between a first position, in which said needle holding members are contained within a diametrical dimension of said barrel, and a second position, in which at least a portion of said needle holding members extend beyond the diametrical dimension of said barrel.

18. An instrument as recited in claim 17, wherein said connecting member is coupled to said barrel to rotate about a first axis that is substantially parallel to the longitudinal axis of said barrel.

19. An instrument as recited in claim 18, wherein said connecting member comprises a pair of arm members, said instrument further comprising an opening device for moving said needle holding members toward and away from one another.

20. An instrument as recited in claim 19, further comprising an operating channel defined in said barrel and extending from said proximal end to said distal end.

21. An instrument as recited in claim 20, further comprising a ligator for tightening a suture loop around a piece of suture material, said ligator being disposed in said operating channel.

22. An instrument as recited in claim 17, further comprising an operating channel defined in said barrel and extending from said proximal end to said distal end.

23. An instrument as recited in claim 22, further comprising a ligator for tightening a suture loop around a piece of suture material, said ligator being disposed in said operating channel.

24. An instrument as recited in claim 17, wherein said connecting member is arcuate.

25. A suturing instrument for causing a needle to pass through anatomical tissue comprising:

an elongated barrel having a distal end and a proximal end;

a handle coupled to said proximal end of said barrel; a shaft extending from said distal end of said barrel, and rotatably mounted within said barrel;

a needle grasping device coupled to a distal end of said barrel and having a longitudinal axis that is offset from a longitudinal axis of said shaft and substantially parallel to said longitudinal axis of said shaft, said needle grasping device being operable with said handle; and a connecting member coupled to and between a distal end of said shaft and said needle grasping device.

26. A suturing instrument as recited in claim 25, wherein said connecting member extends transversely with respect to said barrel.

27. A suturing instrument as recited in claim 26, wherein said connecting member extends substantially perpendicular with respect to a longitudinal axis of said barrel.

28. A method of suturing anatomical tissue using a length of suture material attached to a needle, said method comprising the steps of:

introducing an instrument having a barrel into an area proximate the anatomical tissue;

grasping the needle with a needle grasping device coupled to a distal end of the barrel by a connecting member the needle grasping device having a longitudinal axis that is offset from a longitudinal axis of said barrel and being operable from a proximal end of the barrel;

rotating the connecting member to cause the needle to move in an arcuate path and to cause a tip of the needle to penetrate the anatomical tissue; and releasing the needle from the needle grasping device.

29. A method as recited in claim 28, wherein said rotating step comprises rotating the barrel.

30. A method as recited in claim 28, wherein said rotating step comprises rotating the connecting member relative to the barrel. Please add the following new claim.

31. A method as recited in claim 30 wherein said rotating step comprises rotating the connecting member about an axis substantially parallel to the longitudinal axis of the barrel.

* * * * *